Jan. 15, 1946. C. FUTTERMAN Plant Pat. 668
HYBRID TEA ROSE PLANT
Filed Feb. 9, 1945
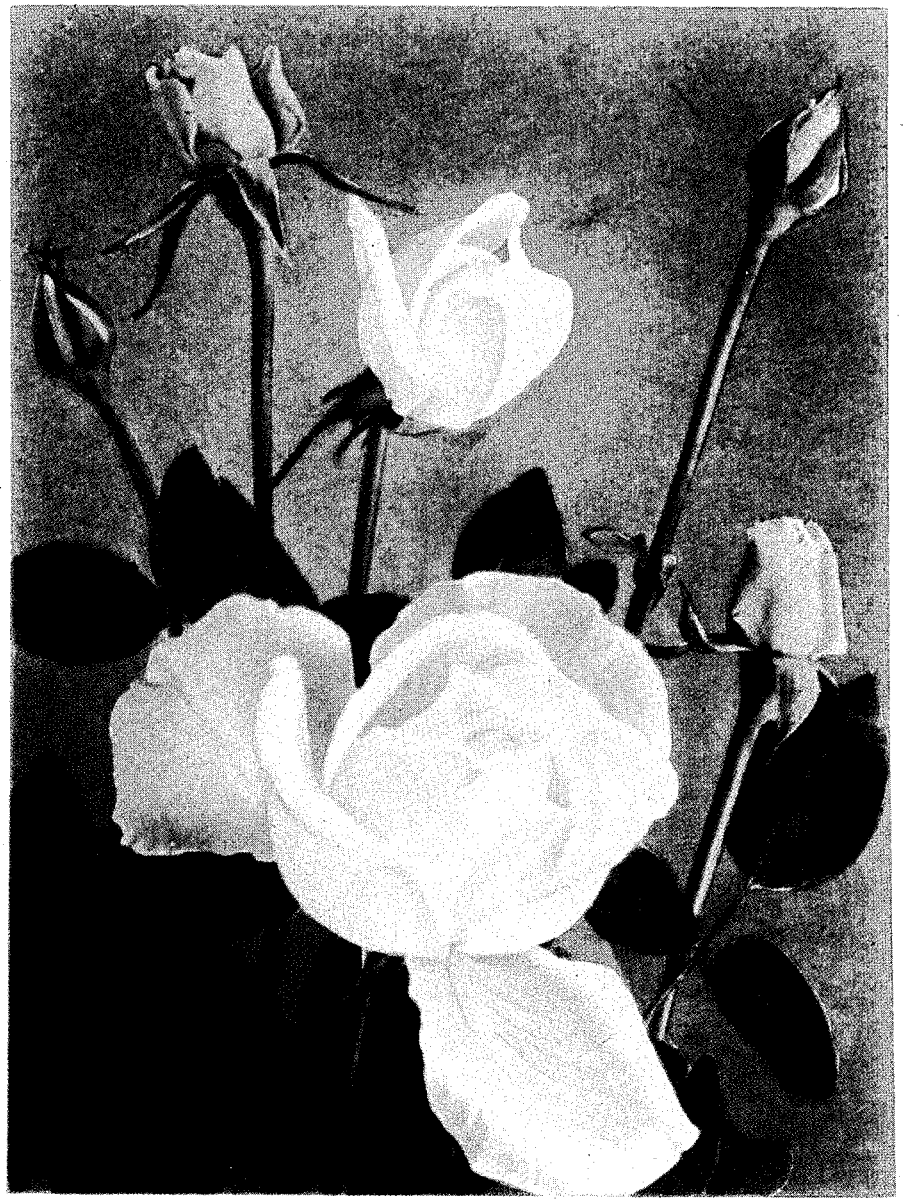
INVENTOR
Charles Futterman
By Orville M. Kile
Plant Patent Agt.

Patented Jan. 15, 1946

Plant Pat. 668

UNITED STATES PATENT OFFICE

668

HYBRID TEA ROSE PLANT

Charles Futterman, Albertson, N. Y.

Application February 9, 1945, Serial No. 577,028

1 Claim. (Cl. 47—61)

My present discovery relates to a new and distinct variety of hybrid tea rose plant which originated as a sport of the variety Better Times (Plant Patent No. 23) in my greenhouses at Albertson, L. I. Although characterized as a white rose, the high center of a full blown flower of this new variety is usually a delicate pink varying greatly in intensity in different specimens from approximating La France Pink (Plate I) to a bare trace of color. The outer petals have none of the pink tint. A most peculiar feature of the variety is the coloring of the bud. Long after the sepals have reflexed and the bud has begun to unfurl, its color is yellow-green. Later it becomes pale greenish yellow blending into a large dark yellow base, no pink being visible until the outer petals open to show the high center. The plant is one of great vigor and the foliage is particularly dark and free from disease.

The accompanying illustration shows one rose with several buds in varying stages of opening, together with foliage and stems. The full blown rose is depicted with the maximum amount of pink found in the flowers of this variety.

Following is a detailed description of this new rose variety, color references being in accord with Ridgway's Color Standards and Nomenclature.

*The plant*

Form: Upright bush.
Growth: Vigorous.
Foliage:
- *Size.*—Small to medium, largest size being about 2½ by 1½ inches.
- *Quantity.*—Abundant.
- *Color.*—Dark green, approximately Dark Cress Green (Plate XXXI).
- *Texture.*—Substantial and leathery. Ribs and veins prominent.
- *Shape.*—Pointed oval.
- *Edge.*—Finely serrated. Serrations are Oxblood Red (Plate I).
- *Number of leaflets.*—3 to 7.

Rachis: Slender; Absinthe Green (Plate XXXI), sometimes red-tinged; grooved above, with occasional prickle and thorn on under side.
Stipules: Smooth; long; narrow and clinging.
Disease resistance: Excellent.
Stems: Long; strong; upright; Forest Green (Plate XVII) to Varley's Green (Plate XVIII).
- *Thorns.*—Very few; russet; irregularly placed. No prickles or needles on stems.

*The flower*

Bud:
- *Size.*—Medium.
- *Form.*—Conical with broad base when first breaking. Rather wedge-shaped just before changing from greenish yellow color.
- *Color.*—Until the bud opens sufficiently to show inner petals, its color is between Light Lumiere Green and Clear Dull Green-Yellow (Plate XVII). Later it becomes Sea-foam Yellow to Sea-foam Green (Plate XXXI) with a large aiglet of Wax Yellow (Plate XVI). In this latter stage the inside of the petals is Pale Calcedonia Yellow (Plate XVII).
- *Sepals.*—Simple; smooth edge; pointed. Curl backward when petals begin to unfurl.
- *Calyx.*—Long; funnel-shaped with broad base; smooth.
- *Peduncle.*—Smooth; frequently bronzed; short, bringing rich foliage close to flower.
- *Opening.*—Slow and perfect.

Bloom:
- *Size.*—Large, with 4 to 5½-inch spread.
- *Borne.*—Singly on long straight stems.
- *Form.*—High-centered and oval-shaped with deep-cupped outer petals. Inner petals frequently give the appearance of a double center. This form is usually retained throughout the life of the bloom although at the very last it may flatten out lightly.
- *Petalage.*—Very double, averaging about 40 petals.
- *Color.*—White overcast with Seafoam Yellow (Plate XXXI), with pale yellow aiglet which is more noticeable on outer petals. Center of flower is of white overcast with varying degrees of pale pink in different specimens, the maximum being approximately La France Pink (Plate I).

Petals:
- *Size.*—Outer petals approximately 2½ by 2½ inches.
- *Arrangement.*—Inner petals tightly grouped to cover stamens, sometimes giving the appearance of a double center. Other petals imbricated.
- *Texture.*—Substantial but with a delicate, shell-like appearance.
- *Form.*—Deep-cupped. Edge slightly scalloped and wavy.
- *Persistence.*—Cling for many days and then drop off cleanly.

Fragrance: More fragrant than any other white rose known to me.

Lasting quality: As a cut flower, unusually splendid.

Reproductive organs: Many stamens and pistils form the center of the flower but are seldom visible because the flower retains its closed high form. *Stamens* are medium in length, yellow in color and are mixed with the petaloids. *Pistils* are short and of uneven lengths, bunched and with stigmas of greenish yellow. *Ovaries* are inclosed in calyx.

*Comparison*

The known variety most nearly like my new variety is the American Pride, subject of Plant Patent No. 49, but the two varieties differ principally in the following points.

1. The pink tint on American pride usually appears on the outer surface of several of the outer petals, while the pink tint on the flowers of my new variety appears in the high center and is not visible until the flower is almost entirely open.

2. The yellowish-green half-open buds of my variety are not found in the variety American Pride.

3. The petals of American Pride quill into triangular shape as the flower opens but petals on my variety seldom quill.

4. My variety has a flower that has a more delicate and transparent appearance than American Pride.

5. Flowers of my variety are very much more fragrant than those of American Pride.

6. Flowers of my variety keep longer when cut.

7. Leaves of my variety average smaller than those of American Pride.

Having thus disclosed my discovery, I claim:

The new and distinct variety of hybrid tea rose plant substantially as shown and described, characterized particularly by its great vigor and disease resistance; its yellow-green half-open buds; the delicate shell-like form and appearance of its pink-tinted white flowers; the unusually abundant fragrance and excellent keeping quality of its flowers.

CHARLES FUTTERMAN.